United States Patent [19]

Konoki et al.

[11] 4,219,492

[45] Aug. 26, 1980

[54] PROCESS FOR MANUFACTURING METHANOL

[75] Inventors: Keizo Konoki, Tokyo; Shinkichi Nozawa, Funabashi, both of Japan

[73] Assignee: Toyo Engineering Corporation, Tokyo, Japan

[21] Appl. No.: 28,385

[22] Filed: Apr. 9, 1979

[30] Foreign Application Priority Data

Apr. 18, 1978 [JP] Japan ................................ 53-44800

[51] Int. Cl.² ............................................. C07C 31/06
[52] U.S. Cl. ................................... 260/449.5; 252/373
[58] Field of Search ....................................... 260/449.5

[56] References Cited

U.S. PATENT DOCUMENTS 3,950,369 4/1976 Gent .................................... 260/449.5

FOREIGN PATENT DOCUMENTS

| | | | |
|---|---|---|---|
| 1580390 | 9/1969 | France ................................... | 260/449.5 |
| 1159035 | 7/1969 | United Kingdom ................... | 260/449.5 |
| 1190071 | 4/1970 | United Kingdom ................... | 260/449.5 |

*Primary Examiner*—Howard T. Mars
*Attorney, Agent, or Firm*—Blanchard, Flynn, Thiel, Boutell & Tanis

[57] ABSTRACT

A process for manufacturing methanol is disclosed, wherein the pressure in the step of preparation of the synthesis gas is selected equal to the pressure in the step of preparation of methanol from the synthesis gas. The operation efficiency of the process is maintained by recycling the methanol-free recycle stream to the reaction zone for methanol synthesis notwithstanding the lower pressure in the step of methanol synthesis.

3 Claims, 1 Drawing Figure

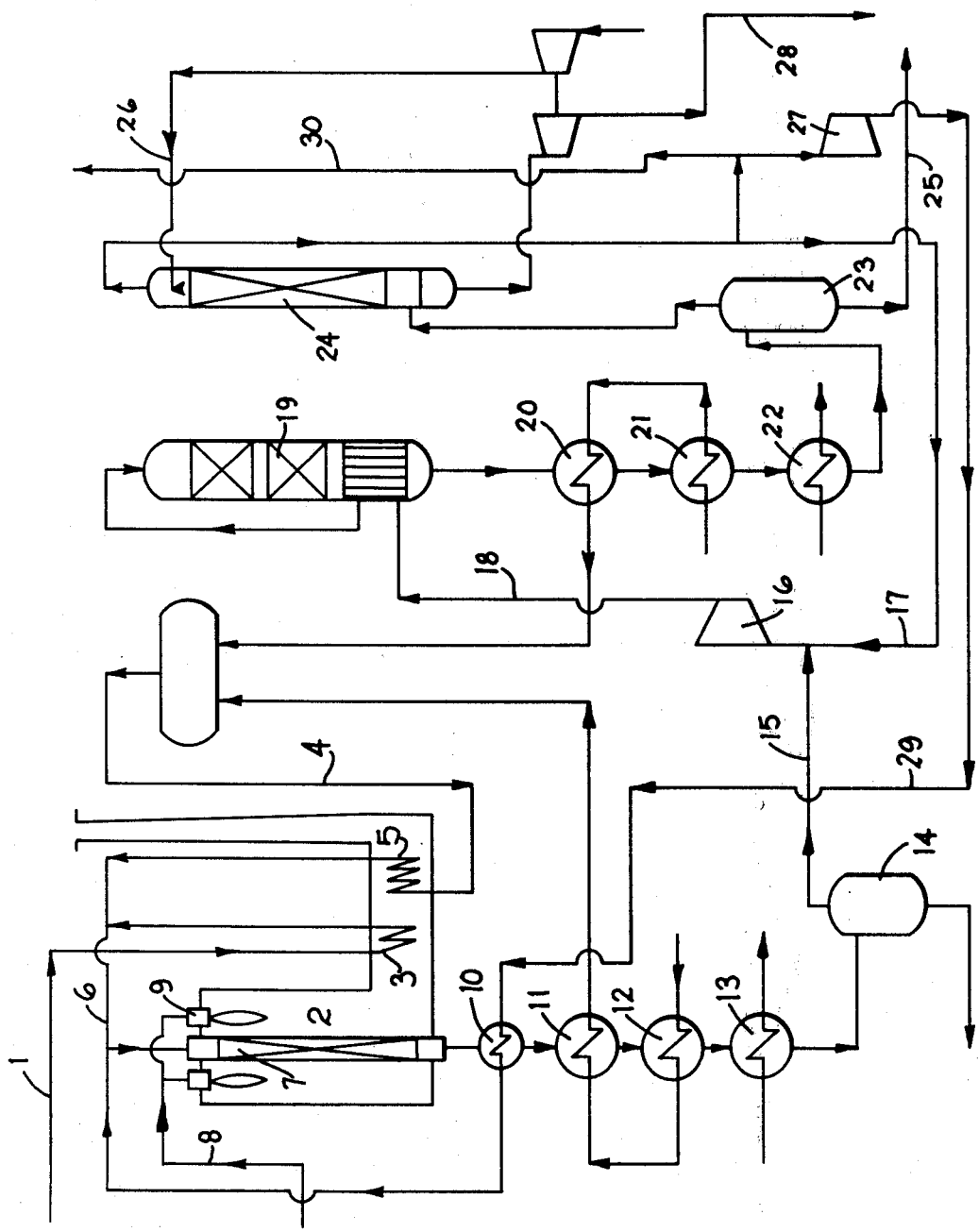

PROCESS FOR MANUFACTURING METHANOL

BACKGROUND OF THE INVENTION

This invention relates to an improvement in the methanol manufacture system.

The demand for methanol is increasing rapidly in recent years for use as a fuel or a source of synthetic protein. Consequently, there is a demand for manufacturing capacity of methanol which is much larger than that required in the age when methanol was used as a chemical material, mainly as a starting material for the preparation of formalin.

In general, methanol is synthethized from natural gases, naphtha or like hydrocarbons as starting material.

Thus, the starting hydrocarbon materials are reacted with steam at elevated temperatures as shown in the formulae (1) and (2) and are converted in this way to CO, $CO_2$ and $H_2$.

$$C_mH_n + mH_2O \rightarrow mCO + (m+n/2)H_2 \quad (1)$$

$$C_mH_n + 2mH_2O \rightarrow mCO_2 + (2m+n/2)H_2 \quad (2)$$

These reactions are characterized by being highly endothermic and volume expansive and are usually carried out in a tubular reactor packed with a catalyst containing nickel and the like as activating components.

As will be described in detail, a synthesis gas is produced in the first step and methanol is prepared from this synthesis gas in the second step. These steps (1) and (2) must be carried out under as high an operating pressure as possible for realizing an elevated energy efficiency of the overall methanol manufacture process comprising the above steps (1) and (2).

More particularly, a certain pressure $P_2$ is required in the reaction for synthesis of methanol from carbon oxides and hydrogen. Suppose that the gasification reaction of the first step is carried out under an operating pressure $P_1$. This pressure $P_1$ is usually smaller than the methanol synthesis pressure $P_2$ ($P_1 < P_2$). As the reactions (1) and (2) are accompanied by volumetric expansion, it is more desirable for the sake of energy saving to elevate the operating pressure prior to the occurrence of such volumetric expansion by using a pressure $P_1$ which is lower than and as close to the pressure $P_2$ as possible.

According to the present invention, the pressure $P_1$ is selected equal to $P_2$ in order to make best use of this feature. Thus, the pressure $P_2$ may be lower than $P_1$ by a pressure decrease $\Delta P$ inevitably caused during the process.

According to the Le Chatelier's law, the progress of the reactions (1) and (2) may be retarded under increased operating pressures.

According to the same law, since the reactions are endothermic, the higher the reaction temperatures, the reactions will proceed more and more towards the right.

This fact indicates that the disadvantages brought about by the increased gasification pressure in the first step may be eliminated by using the higher reaction temperatures.

Thus, in order to promote the reactions (1) and (2), the following technological difficulties must be overcome.

As described above, the quantity of heat absorbed during the reactions must be increased for compensating the pressure increase in the reactions. Therefore, a multiplicity of tubular reactors or reaction tubes are provided in a combustion furnace of a large capacity in such a manner that the furnace interior may be maintained at higher temperatures by combustion of more fuel outside of the tubular reactors and the heat thus generated may be transmitted to the reactants through the tube wall. This means that the tube wall must be capable of withstanding the elevated temperatures and pressures.

The gaseous mixtures leaving these tubular reactors are typically maintained at a pressure less than 20 kg/cm²G and a temperature less than 850° C. According to the present invention, in order to elevate the pressure $P_1$, the reaction pressure and temperature are selected to be 30 to 50 kg/cm²G and 850° to 1050° C., respectively.

To this end, use is made preferably of a material such as heat-resistant steel of the 25Cr-35Ni series with or without addition of Nb, Co or W having high-temperature creep strength superior to the heat resistant steel of the 25Cr-20Ni series conventionally used as materials for reaction tubes.

The second step of the present process in which carbon monoxide and carbon dioxide are reacted catalytically to form methanol is shown by the formulas $$CO + 2H_2 \rightarrow CH_3OH \quad (3)$$

$$CO_2 + 3H_2 \rightarrow CH_3OH + H_2O \quad (4)$$

As is apparent from these formulae, these reactions exhibit volumetric reduction and must necessarily be carried out under elevated pressures.

Conventionally, methanol synthesis was carried out under an elevated pressure, e.g. at 300 Kg/cm²G. Recently, with development of a catalyst of higher catalytic activity, the synthesis pressure of 50 to 100 Kg/cm²G has come to be employed in general.

According to present invention, the synthesis pressure is decreased further to 30 to 50 Kg/cm²G in order to make the gasification pressure equal to the methanol synthesis pressure, as described above. In addition, the methanol contained in the gas recycled towards the methanol synthesis zone is removed by scrubbing with water for compensating for the reduction in efficiency caused by reduction of the synthesis pressure.

The methanol concentration of the gaseous mixture leaving the methanol synthesis reactor is decreased with decrease in the synthesis pressure. In the conventional system, the methanol concentration of the effluent gaseous mixture from the reactor amounted approximately to 0.5%. According to the present invention, the effluent gaseous mixture from the reactor is cooled for separation and recovery of methanol and further scrubbed with water for decreasing the methanol concentration substantially to 0%. In this way, the amount of the unreacted gaseous mixture in circulation may be prevented from increasing and there occurs no decrease in the energy efficiency of the overall manufacture process.

The residual methane in the gaseous mixture from the first or gasification step and the methane by-produced by the reactions shown by the formulae (5) and (6) in the second or methanol synthesis step act as inert gas in the second step and, if such methane is allowed to circulate in the reactor loop of the second step without partial discharge of the recirculated gas, there occurs methane accumulation in the second step with resulting decrease in the effective pressures of carbon monoxide, carbon dioxide and hydrogen and eventual termination of the reactions of the formulae (3) and (4).

$$CO + 3H_2 \rightarrow CH_4 + H_2O \tag{5}$$

$$CO_2 + 4H_2 \rightarrow CH_4 + 2H_2O \tag{6}$$

Such inconvenience may generally be overcome by partial discharge of the recirculated gas from the second step. This method is not desirable because the valuable carbon monoxide, carbon dioxide and hydrogen under elevated pressures will be lost along with the methane. Usually, this purge gas, that is, the discharged gaseous mixture, is used as a fuel gas.

According to the present invention, this purge gas is recycled partly or wholly to the process gas stream supplied to the first step for reforming the methane contained therein to hydrogen and carbon oxides for redelivery into the second step.

If nitrogen or other impurities are contained in larger quantities in the feedstock to the first step, recirculation of the purge gas to the first step would not be so effective and hence a considerable amount of the purge gas would have to be employed as fuel gas according to the conventional practice.

BRIEF DESCRIPTION OF THE DRAWING

The drawing is a flow diagram showing the process of the present invention.

DESCRIPTION OF THE PREFERRED EMBODIMENT

The gaseous feedstock supplied under pressure from pipe 1 and containing the hydrocarbon material is preheated in a heat exchanger 3 by indirect heat exchange with combustion gases from a heating furnace 2. On the other hand, steam is supplied through pipe 4 and superheated in a heat exchanger 5 in a similar manner. The gaseous feedstock and the steam are mixed together in a pipe 6 and introduced into a reforming tube 7. The reformer tube or tubular reactor 7 is fabricated from heat-resistant material and packed in its inside with a catalyst containing nickel as effective catalytic ingredients. Although only one tubular reactor 7 is shown in the drawing for the sake of simplicity, it is to be understood that a multiplicity of similar tubes 7 are actually provided in the combustion furnace 2 and supplied with the feedstock and steam through a manifold, not shown, connected to the pipe 6.

The fuel for heating the tubes 7 is supplied form a pipe 8 to burners 9 for combustion.

The gaseous mixture leaving the tubes 7 is cooled as it travels through a preheater 10 for the process recycle gas, a waste heat boiler 11, a preheater for feed water 12 and a cooler 13. The mixture thus cooled is then supplied into a condensate separator 14 for separation mainly of condensed water and then supplied to the second step of the manufacture process through a pipe 15.

The gaseous mixture from pipe 15 is supplied through a pipe 17 into a circulator 16 and thence into a methanol synthesis reactor 19 along with a methanol-free gaseous stream recycled by a pipe 17. The reactions of the formulae (3) and (4) are carried out catalytically in the reactor 19. The methanol-containing gaseous mixture leaving the reactor 19 is than supplied through a waste heat boiler 20, a preheater for feed water 21, a cooler 22, and a crude methanol separator 23 into a scrubbing tower 24 where the scrubbing water is supplied through a pipe 26. The gaseous stream thus separated from methanol is recycled by way of tube 17 and the circulator 16 back into the reactor 19.

The highly condensed crude methanol obtained at the separator 23 and the aqueous solution of methanol from the scrubbing tower 24 are supplied by way of pipes 25 and 28, respectively, towards a methanol purification step, not shown.

In the process flow sheet, part of the methanol-free gas stream from the scrubbing tower 24 is supplied as a second recycle stream to a circulator 27 where the pressure of the recycle stream is elevated by an amount equal to the pressure drop caused in the course of the first and second steps. The recycle stream is then supplied again into the tubes 7 by way of a pipe 29 and the preheater 10. The methanol-free gas which is not supplied to the circulator 27 is removed from the process by a pipe 30.

The present invention will be explained further by referring to the Examples.

EXAMPLE 1

The natural gas at a pressure of 4.9 kg/cm²G was pressurized and steam reformed by the tubular reactor 7. The pressure and the temperature of the reformed gas obtained at the exit from the tubular reactor 7 were 39.3 kg/cm²G and 930° C., respectively. The composition in vol. % of the reformed gas was as follows.

| CO, 15.01; | CO$_2$, 7.23; | H$_2$, 72.20; |
|---|---|---|
| CH$_4$, 4.21; | N$_2$, 1.35. | |

The hot reformed gas was cooled with heat recovery as described above and its pressure and temperature were lowered to 36.3 kg/cm²G and ambient temperature, respectively, while the condensates were removed. The reformed gas was then supplied along with the first recycle stream into the circulator 16 where the gas pressure was raised to 40.4 kg/cm²G. The gaseous mixture was then supplied into the reactor 19.

The composition in vol. % of the gaseous mixture consisting of the reformed and recycled gases was as follows.

| CO, 5.87; | CO$_2$, 2.61; | H$_2$, 76.36; |
|---|---|---|
| CH$_4$, 11.46; | N$_2$, 3.59; | H$_2$O, 0.02; |
| CH$_3$OH, 0.08. | | |

Methanol was produced on the catalyst contained in the reactor 19. The temperature and pressure of the gaseous mixture leaving the terminal point of the catalyst bed were 270° C. and 38.4 kg/cm²G, respectively, and had a methanol content equal to 1.75 vol. %.

The gaseous mixture was cooled to 40° C. and the methanol was condensed and removed in the separator 23. Thus, the methanol content of the gaseous mixture leaving the separator 23 was reduced to 0.72 vol. %. The gaseous mixture was then scrubbed with water in the scrubbing tower 24 where the methanol was further removed. The methanol content of the mixture leaving the scrubbing tower was 0.08 vol. %.

By this scrubbing operation, the aqueous solution of methanol with the methanol contents of 60 wt.% was obtained in the pipe 28.

According to the present invention, methanol is removed from the methanol-containing gaseous mixture by condensation and the resulting stream is scrubbed with water for further removal of methanol in the scrubbing tower. Thus, the substantially methanol-free recycle gas is fed back into the reactor 19. In this way, the conversion rate to methanol in the reactor 19 may be improved considerably and the methanol synthesis process can be executed without any practical hindrance despite the lower pressure employed in the methanol synthesis reactor.

The aqueous solution of methanol obtained by water scrubbing is mixed with the crude methanol obtained upon condensation by cooling and supplied to a process wherein pure methanol may be yielded by distillation. The presence of water in the aqueous solution of methanol is effective and highly advantageous in that relative volatility of the lower boiling impurities contained in the crude methanol to methanol may become higher.

Moreover, according to the present invention, a compressor used in the methanol synthesis step of the conventional process for methanol synthesis gas may be dispensed with. Therefore, the quantity of natural gas used as fuel and feedstock per unit quantity of product can be reduced considerably.

The following Table shows, for comparison sake, the quantity of natural gas required in the inventive process and that required in the conventional process where the synthesis pressure is 100 kg/cm$^2$G.

In the Table, the quantity of the natural gas equal to 10$^6$ Kcal per each ton of methanol is denoted as unity.

TABLE

|  | Natural gas as feedstock | Natural gas as fuel | Total | Note |
|---|---|---|---|---|
| Conventional | 7.902 | 0.678 | 8.580 |  |
| Inventive | 7.953 | 0.380 | 8.333 | 3% decrease |

EXAMPLE 2

The hot reformed gas obtained was cooled by heat recovery as in the preceding Example. Carbon dioxide ($CO_2$) was added to the resulting cooled gas for adjusting the composition in vol. % to: CO, 12.81; $CO_2$, 10.36; $H_2$, 72.48; and $CH_4$, 4.35.

The reformed gas thus added with $CO_2$ was supplied as a synthesis gas to the inlet of the circulator at an ambient temperature and a pressure of 38.9 kg/cm$^2$G. The synthesis gas was elevated in pressure in the circulator along with the first recycle gas to a pressure of 43.0 kg/cm$^2$G and then supplied into the methanol synthesis reactor.

The composition in vol. % of the gaseous mixture consisting of the synthesis gas and the recycle gas was: CO, 9.35; $CO_2$, 8.36; $H_2$, 73.98; $CH_4$, 8.09; $H_2O$, 0.10; and $CH_3OH$, 0.08.

The temperature and pressure of the gaseous mixture leaving the catalyst bed of the reactor in which methanol was produced were 270° C. and 38.9 kg/cm$^2$G, respectively. The mixture had a methanol content equal to 3.06 vol. %.

The gaseous mixture was then cooled to 40° C. and methanol was separated therefrom by condensation. The methanol content of the mixture was thus lowered to 0.58 vol. %. The mixture was then subjected to water scrubbing for further removal of methanol, and the methanol content of the mixture was thus lowered to 0.08 vol. %.

The aqueous solution of methanol with a methanol content equal to 60 wt. % was obtained by this scrubbing with water. Most of the gaseous mixture thus scrubbed with water was recirculated to an intermediate stage of the compressor for the natural gas used as feedstock. However, a minor amount of the gaseous mixture was discharged from the process for preventing accumulation of methane in the second step.

According to the present Example, the motive power used in vain for gas purging can be used for process operation with resulting saving in motive power.

In the present Example, the quantity of the natural gas required for manufacture of 1 ton of methanol is slightly larger than that in the preceding Example and amounts to 8.919×10$^6$ Kcal. However, on the other hand, 0.96 ton of steam at 100 kg/cm$^2$ and 482° C. is by-produced per 1 ton of methanol.

What is claimed is:

1. A process for manufacturing methanol, which comprises the steps of:

feeding a gaseous hydrocarbon feedstock and steam into a steam reforming reactor containing steam reforming catalyst and effecting a steam reforming reaction, at a temperature of from 850° to 1050° C., at a pressure of 30 to 50 Kg/cm$^2$ gauge, to produce a reformed gas mixture containing water vapor, $H_2$, CO and $CO_2$; then cooling said reformed gas mixture to condense the water vapor and separating the condensed water vapor from the remainder of said reformed gas mixture to obtain a water-free reformed gas mixture which is at ambient temperature and at about the same pressure as the pressure in said steam reforming reactor; feeding said water-free reformed gas mixture into a methanol synthesis reactor without materially changing the pressure thereof and in said methanol synthesis reactor contacting said water-free reformed gas mixture with a methanol synthesis catalyst, at a pressure substantially equal to the pressure in said steam reforming reactor, to produce a methanol-containing reaction product gas; then cooling said methanol-containing reaction product gas to condense part of the methanol contained therein and then separating the condensed methanol from the remainder of said methanol-containing reaction product gas; removing the condensed methanol as a first product of the process; then flowing said remainder of said methanol-containing reaction product gas into a scrubbing column and therein contacting same with liquid water to condense and dissolve in the water substantially all the methanol present in said remainder of said methanol-containing reaction product gas; removing from said scrubbing column the aqueous solution of methanol as a second product of the process; separately removing from the scrubbing column a substantially methanol-free gas recycle stream; separating a first portion of said methanol-free gas recycle stream and feeding same into said water-free reformed gas mixture which is fed into said methanol synthesis reactor; separating another portion of said methanol-free gas recycle stream and increasing the pressure and temperature thereof to approximately the temperature and pressure in said steam reforming reactor and then feeding same into said steam reforming reactor along with said gaseous hydrocarbon feedstock and said steam.

2. A process as claimed in claim 1 in which said another portion of said methanol-free gas recycle stream is flowed in indirect heat exchange relationship with said reformed gaseous mixture immediately after same has been discharged from the steam reforming reactor in order to cool said reformed gaseous mixture and to increase the temperature of said another portion of said methanol-free gas recycle stream.

3. A process as claimed in claim 1 or claim 2 in which said steam is generated by flowing water in indirect heat exchange relationship with said reformed gas mixture discharged from said steam reforming reactor and with said methanol-containing reaction product gas discharged from said methanol synthesis reactor.

* * * * *